United States Patent [19]

Golub et al.

[11] Patent Number: 4,689,213

[45] Date of Patent: Aug. 25, 1987

[54] METHOD AND COMPOSITION FOR TREATING BRONCHOSPASTIC AIRWAY DISEASES

[75] Inventors: Allyn Golub, Coral Gables; Leslie Hendeles, Gainesville, both of Fla.

[73] Assignee: Key Pharmaceuticals, Inc., Miami, Fla. ; by said Allyn Golub

[21] Appl. No.: 790,408

[22] Filed: Oct. 23, 1985

Related U.S. Application Data

[63] Continuation-in-part of Ser. No. 754,694, Jul. 15, 1985, abandoned.

[51] Int. Cl.$^4$ ............................................. A61K 31/275
[52] U.S. Cl. ................................... 424/45; 514/520; 514/826
[58] Field of Search .................. 514/520, 826; 424/45

[56] References Cited

PUBLICATIONS

Alfred G. Gilman et al., Goodman and Gilman's The Pharmacological Basis of Therapeutics, Sixth Edition, pp. 153–154 and 166–172.
E. W. Russi, "Modification of Allergic Bronchoconstriction by a Calcium Antagonist: Mode of Action", Am Rev Respir Dis, 1983; 127:675–679.
E. W. Russi et al., "Calcium and Calcium Antagonists in Airway Disease—A Review", Chest, vol. 86, pp. 475–482, Sep. 1984.
E. W. Russi et al., "Comparative Modification of Antigen-Induced Bronchoconstriction by the Calcium Antagonists Nifedipine and Verapamil", Chest, Jul. 1985, 88, p. 74.
Tahir Ahmed et al., "Comparative Effects of Oral and Inhaled Verapamil on Antigen-Induced Bronchoconstriction", Chest, Aug. 1985, 88, p. 176.
Aml Lever, "Nifedipine Enhances the Bronchodilator Effect of Salbutamol", Thorax, 1984; 3:576–578.
"Correspondence", Thorax, 1985, 40: 399–400.
Medline Search Report–80/85/May, "Calcium Channel Blockers Aerosol Dosage Form and Nebulized Dosage Form".
Hertz et al.–Chemical Abstracts, 100:17372d, 1984.
S. Y. So, "Effect of Calcium Antagonists on Allergen-Induced Asthma", Clinical Allergy, 1982, vol. 12, pp. 595–600.
K. R. Patel, "The Effect of Inhaled Verapamil on Allergen-Induced Bronchoconstriction", Clinical Allergy, 1983, vol. 13, pp. 119–122.
T. Ringqvist, "Effect of Verapamil in Obstructive Airways Disease", Europ. J. Clin. Pharmacol, 7, 61–64 (1974).
K. R. Patel, "Calcium Antagonists in Exercise-Induced Asthma", British Medical Journal, vol. 282, 932, Mar. 1981.
Valentin T. Popa, "The Effect of Inhaled Verapamil on Resging Bronchial Tone and Airway Contractions Induced by Histamine and Acetylcholine in Normal and Asthmatic Subjects", Am. Rev. Respir. Dis. (1984), 130: pp. 1006–1013.
E. McIntyre, "Inhaled Verapamil in Histamine-Induced Bronchoconstriction", J Allergy Clin Immunol, 71:375 (1983).
C. Advenier, "Sodium Cromoglycate, Verapamil and Nicardipine Antagonism to Leukotriene D Bronchoconstriction", Br. J. Pharmac. (1983), 78, pp. 301–306.
K. R. Patel, "The Effect of Verapamil on Histamine and Methacholine-Induced Bronchoconstriction", Clinical Allergy, 1981, vol. II, pp. 441–447.
Eric W. Russi, "Today's Practice of Cardiopulmonary Medicine", Chest, vol. 86, pp. 475–482, Sep. 1984.
Elliott Middleton, Jr., "Airway Smooth Muscle, Asthma, and Calcium Ions", J. Allergy Clin Immunol., 73:643 (1984).
Eh Walters, "Effects of Calcium Channel Blockade on Histamine Induced Bronchoconstriction in Mild Asthma", Thorax, 1984; 39:572–575.

Primary Examiner—Leonard Schenkman
Attorney, Agent, or Firm—John J. Maitner; Stephen I. Miller; James R. Nelson

[57] ABSTRACT

Bronchospastic diseases characterized by airway hyperreactivity are treated by administration of the calcium channel blocker gallopamil. Unlike other calcium channel blockers, the effective dose of gallopamil is small enough that undesirable side effects are not present.

10 Claims, No Drawings

METHOD AND COMPOSITION FOR TREATING BRONCHOSPASTIC AIRWAY DISEASES

CROSS REFERENCE TO RELATED APPLICATION

The present application is a continuation-in-part of Ser. No. 754,694 filed July 15, 1985 now abandoned.

BACKGROUND OF THE INVENTION

1. Field of the Invention

The present invention is directed to the treatment of bronchospastic airway diseases, especially reversible airway hyperreactivity, with a calcium channel blocker. More particularly, the invention is concerned with such treatment using the calcium channel blocker gallopamil.

2. Description of the Prior Art

The compound gallopamil is a known calcium channel blocker. Like other calcium channel blockers such as nifedipine, diltiazim and verapamil, gallopamil is used in cardiovascular therapy. Verapamil, diltiazim and nifedipine have been tested for possible use as active therapeutic agents in treating reversible airway hyperreactivity. however, the dosages necessary to obtain the desired airway hyperreactivity reduction have resulted in undesirable side effects such as broncho spasm. Also, the dosages have been as high or higher than the dosages used in cardiovascular therapy.

SUMMARY OF THE INVENTION

In a first aspect, the present invention is directed to a method for treating a bronchospastic disease characterized by airway hyperreactivity comprising administering to a subject an amount of gallopamil sufficient to reduce airway hyperreactivity, particularly via a pulmonary route.

A second aspect of the invention involves a composition for treating a bronchospastic disease characterized by airway hyperreactivity, comprising an amount of gallopamil effective to reduce airway hyperreactivity and a pharmaceutically acceptable carrier, adjuvant or excipient therefor, especially in a form suitable for aerosol administration.

DETAILED DESCRIPTION OF THE INVENTION

The present invention concerns treatment of bronchospastic airway diseases, especially reversible airway hyperreactivity, by administration of the calcium channel blocker gallopamil (5-[[2-(3,4-dimethoxyphenyl)ethyl]methylamino]-2-isopropyl-2-[3,4,5-trimethoxyphenyl]pentanonitrile hydrochloride). The term "gallopamil" is intended to cover useful derivatives such as other pharmaceutically acceptable salts, non-salt forms, etc. The term "reversible airway hyperreactivity" refers to conditions such as allergen and exercise-induced asthma, etc., which result in reversible blockage of the air passages. So-called irreversible airway conditions such as emphysema also involve reversible aspects. It is expected that the present invention will be most useful in treatment of chronic conditions.

It is preferred that the gallopamil be administered in a pulmonary fashion, i.e., directly to the lungs in the form of an aerosol. Such aerosol administration can be in the form of a nebulized saline solution. Generally, the solution can include about ½-1% by weight gallopamil in 0.4% saline. Solubility of gallopamil in the solution is improved by addition of solubilizers such as ethanol and propylene glycol, both in amounts of about 4% by weight, for example. pH adjustment should be accomplished with sodium bicarbonate. Alternatively, the gallopamil could be dispersed in freon and administered through a metered dose inhaler. It is particularly desirable to use a metered dose inhaler with an inhaling device such as that disclosed in Sackner et al. U.S. Pat. No. 4,484,577, the disclosure of which is incorporated herein by reference.

Oral administration in the form of tablets or capsules is possible, but may be disadvantageous because higher dosages are required, possibly leading to undesired cardiovascular effects. Parenteral and topical administration also are possible, although not preferred because of inconvenience and higher required dosage. Parenteral administration likely would be most useful in emergency situations, but it is contemplated that the present invention will be most useful in a preventative manner or for relief via self-administration.

When the gallopamil is delivered via a nebulized saline solution, enough solution should be used to provide a gallopamil dose of about 1-20 mg, preferably 1-10 mg. This dosage can be repeated up to three or four times per day. When a metered dose inhaler is used in place of the nebulization, the dose of gallopamil may be reduced to about one tenth of the nebulized dose, preferably about 0.1-1 mg of gallopamil.

As noted above, a nebulized aerosol composition can be made using 0.4% saline as the carrier for gallopamil to be delivered in a nebulized manner. Suitable solubilizers and other presently known components for aerosol compositions can be used if necessary or desired. Carrier gases presently known for use in metered dose inhalers, such as freon, are suitable for administering gallopamil from a metered dose inhaler.

EXAMPLE

Subjects documented to be susceptible to intermittent asthma attacks due to causes such as allergens, exercise, smoke, etc., are selected. The dose ($PD_{20}$) of methacholine (an asthma inducer) necessary to produce a 20% decrease in forced expired volume in one second ($FEV_1$) is determined for each subject, with each subject having a $PD_{20}$ of less than 12 mg/ml. Administration of nebulized gallopamil (3 ml of a solution containing amounts of gallopamil varying from 1-20 mg, 4% ethanol and 4% propylene glycol in sterile saline, pH adjusted to 6 with sodium bicarbonate) increases the $PD_{20}$ for methacholine by 2-3 fold, thus showing significant reduction in airway hyperreactivity. There is no significant cardiovascular activity and undesired side effects such as bronchospasms are not present. Approximately 10 times as much verapamil does not produce as large a $PD_{20}$ increase, and bronchospasm results from higher dosages.

What is claimed is:

1. A methd for treating a bronchospastic disease characterized by airway hyperreactivity comprising administering to a subject an amount of gallopamil sufficient to reduce airway hyperreactivity wherein the gallopamil is administered in aerosol form via a pulmonary route.

2. The method of claim 1, wherein the gallopamil is administered from a metered dose inhaler.

3. The method of claim 1, wherein the gallopamil is administered in a nebulized form.

4. The method of claim 2, wherein the amount of gallopamil administered is about 0.1–1 mg.

5. The method of claim 3, wherein the amount of gallopamil administered is about 1–20 mg.

6. A composition for treating a bronchospastic disease characterized by airway hyperreactivity, comprising an amount of gallopamil effective to reduce airway hyperreactivity and a pharmaceutically acceptable carrier, adjuvant or excipient therefor wherein the composition is in a form suitable for aerosol administration.

7. The composition of claim 6, wherein the composition is in a form suitable for administration through a metered dose inhaler.

8. The composition of claim 7, wherein the composition is in a form suitable for administration via nebulization.

9. The composition of claim 7, wherein about 0.1–1 mg of gallopamil is administered.

10. The composition of claim 8, wherein about 1–20 mg of gallopamil is administered.

* * * * *